US00PP25642P2

(12) United States Plant Patent
Yates

(10) Patent No.: US PP25,642 P2
(45) Date of Patent: Jun. 23, 2015

(54) ***BEGONIA* PLANT NAMED 'YANTANA'**

(50) Latin Name: ***Begonia* hybrid**
Varietal Denomination: YANTANA

(71) Applicant: Frederic C. Yates, Congleton (GB)

(72) Inventor: Frederic C. Yates, Congleton (GB)

( * ) Notice: Subject to any disclaimer, the term of this patent is extended or adjusted under 35 U.S.C. 154(b) by 84 days.

(21) Appl. No.: 13/998,506

(22) Filed: Nov. 6, 2013

(51) Int. Cl.
*A01H 5/02* (2006.01)

(52) U.S. Cl.
USPC ..... Plt./343

(58) Field of Classification Search
USPC ..... Plt./343
CPC ..... A01H 5/0238; A01H 5/02; A01H 5/00
See application file for complete search history.

*Primary Examiner* — Kent L Bell
(74) *Attorney, Agent, or Firm* — Penny J. Aguirre

(57) ABSTRACT

A new cultivar of hybrid *Begonia* named 'YANTANA', characterized by its large flowers with light yellow-orange centers and dark pinkish red margins in color with a high degree of upward and horizontal facing flowers, its semi-double sterile male flowers and single female flowers with modified stigmas that have been observed to lack both self-pollination and cross-pollination, its flowers that are long-lived due to lack of pollination making it useful for use in flowerbeds, containers, and baskets, and its compact, mounded and well-branched habit without cane production in its first year of growth.

3 Drawing Sheets

Botanical classification: *Begonia* hybrid.
Cultivar designation: 'YANTANA'.

RELATED APPLICATIONS

This application is related to U.S. Plant Patent applications filed for cultivars derived from the same breeding program entitled *Begonia* Plant named 'YASPWHIT' (U.S. Plant Pat. No. 23,281), *Begonia* Plant Named 'YASPMON' (U.S. Plant Pat. No. 20,846), *Begonia* Plant Named 'YASPRINK' (U.S. Plant Pat. No. 23,266), and *Begonia* Plant Named 'YASPED' (U.S. Plant Pat. No. 22,412).

BACKGROUND OF THE INVENTION

The present invention relates to a new and distinct cultivar of *Begonia* plant, botanically an interspecific hybrid that includes *Begonia boliviensis* hybrids in its parentage. The new cultivar is known as *Begonia* 'YANTANA' and will be referred to hereafter by its cultivar name, 'YANTANA'. 'YANTANA' is a new cultivar of *Begonia* that is particular useful for use in flowerbeds, containers, and hanging baskets.

The new cultivar was derived from a controlled breeding program conducted by the inventor at his nursery in Congleton, Cheshire, United Kingdom. The overall purpose of the breeding program is to make selections of *Begonia* plants to produce good basket and patio plants. 'YANTANA' was selected in the Inventor's greenhouse in July of 2008 as a single unique plant from amongst the seedlings derived from a cross made in 2007 between unnamed *Begonia* plants of hybrid origin from the Inventor's breeding program as the female and male parents.

Asexual propagation of the new cultivar was first accomplished by stem tip cuttings in Congleton, Cheshire, United Kingdom in fall of 2011 by the Inventor. Asexual propagation by stem tip cuttings has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'YANTANA' as a new and distinct cultivar of *Begonia*.

1. 'YANTANA' exhibits large flowers with light yellow-orange centers and dark pinkish red margins in color.
2. 'YANTANA' exhibits semi-double sterile male flowers and single female flowers with modified stigmas that have been observed to lack both self-pollination and cross-pollination.
3. 'YANTANA' exhibits flowers that are long-lived due to lack of pollination making it useful for use in flowerbeds, containers, and baskets.
4. 'YANTANA' exhibits flowers that have a high degree of upward and horizontal facing flowers.
5. 'YANTANA' exhibits a compact, mounded and well-branched habit without cane production in its first year of growth.

The female parent of 'YANTANA' differs from 'YANTANA' in having pink to pale rose colored flowers with many veins and tepal edges that are ragged. The male parent is similar to 'YANTANA' in plant habit but differs from 'YANTANA' in having pinkish red flowers. 'YANTANA' can be most closely compared to cultivars from the same breeding program: 'YASPWHIT', 'YASPMON', 'YASPRINK', and 'YASPED'. 'YASPWHIT' differs from 'YANTANA' in having white flowers lightly flushed with pink with broader tepals. 'YASPMON' differs from 'YANTANA' in having flowers that are pink-orange in color and a more trailing plant habit. 'YASPRINK' differs from 'YANTANA' in having pink flowers. 'YASPED' differs from 'YANTANA' in having dark red flowers, a more pendulous plant habit and in having a more vigorous growth habit.

BRIEF DESCRIPTION OF THE DRAWING

The accompanying colored photograph illustrates the overall appearance and distinct characteristics of the new *Bego-*

*nia*. The photograph was taken of a plant approximately three months in age as grown in a 25-cm container in an unheated greenhouse under ambient light in Congleton, Cheshire, United Kingdom.

Figure 1:
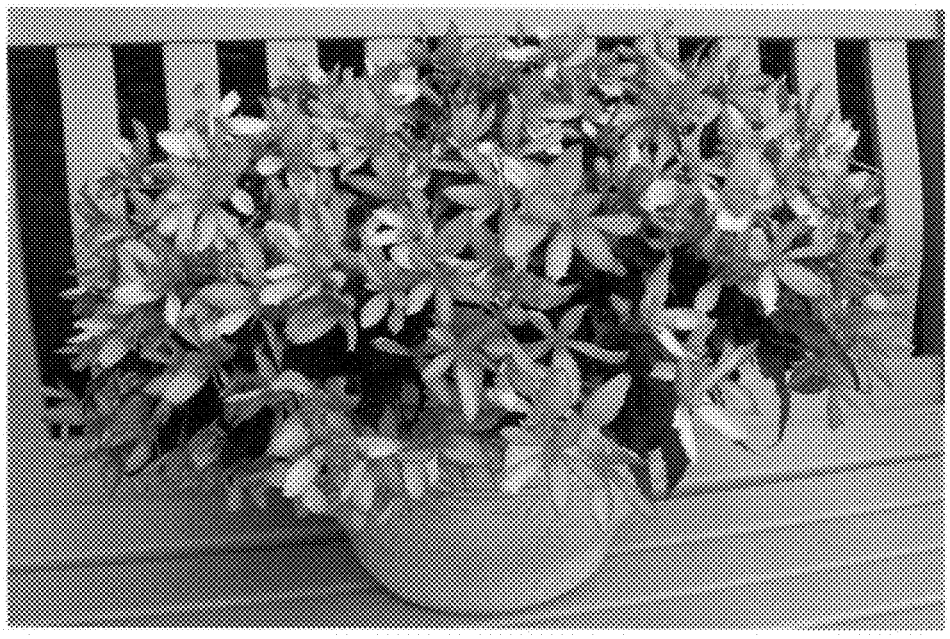

The photograph in FIG. 1 provides a side view of 'YANTANA' in bloom.

Figure 2:
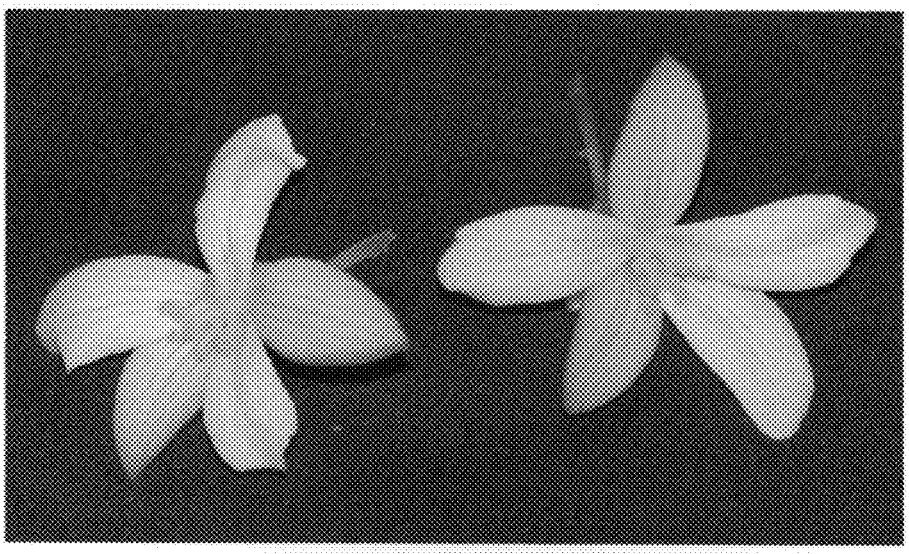

The photograph in FIG. 2 provides a close-up view of the female flowers.

Figure 3:
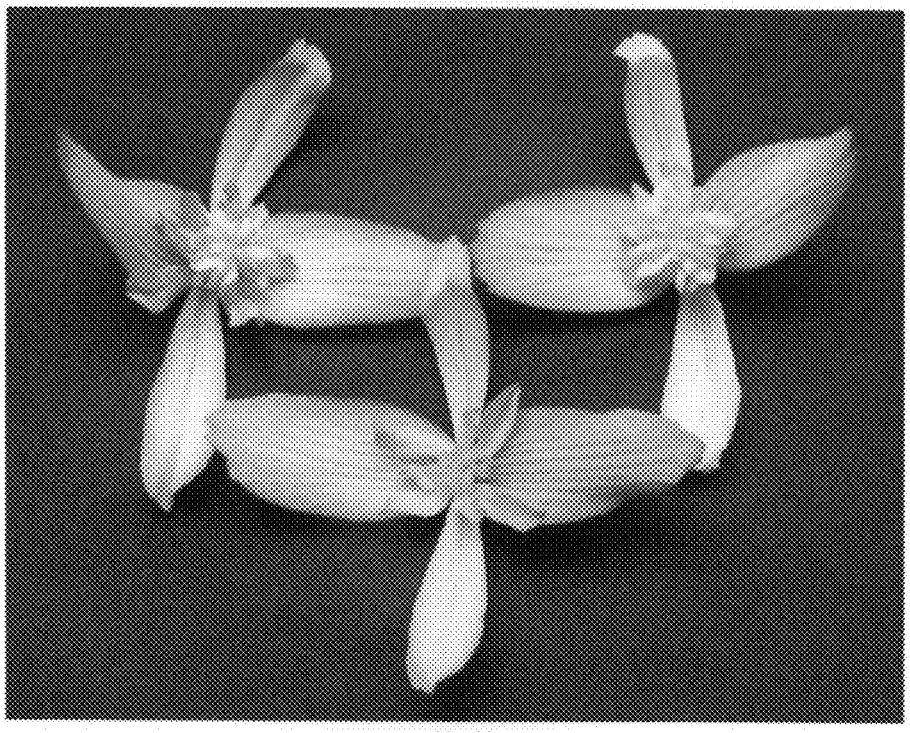

The photograph in FIG. 3 provides a close-up view of the male flowers.

Figure 4:
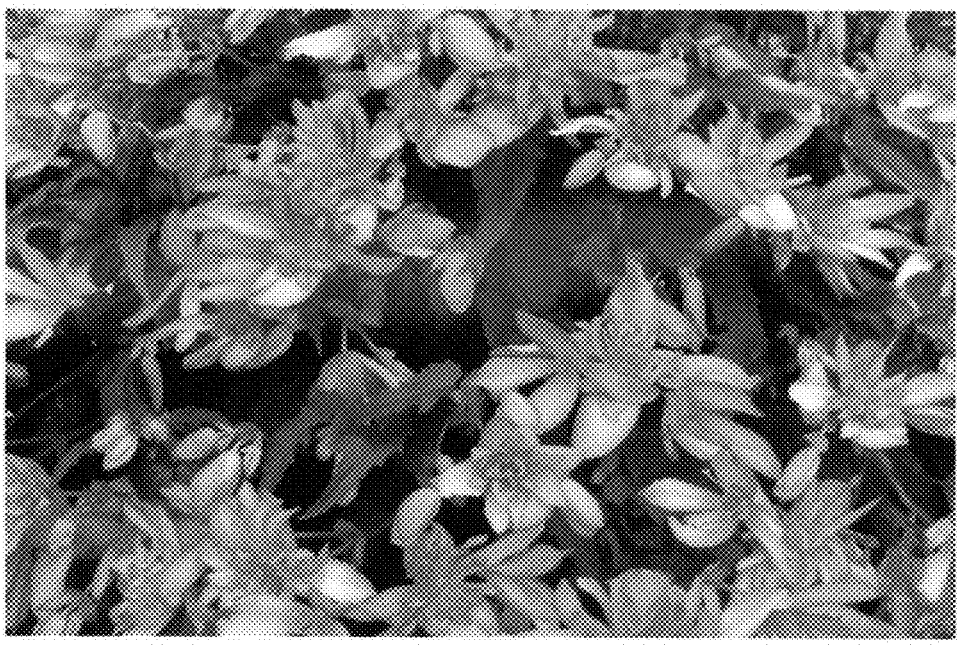

The photograph in FIG. 4 provides a close-up view of both the female and male flowers.

The colors in the photograph may differ slightly from the color values cited in the detailed botanical description, which accurately describe the colors of the new *Begonia*.

DETAILED BOTANICAL DESCRIPTION OF THE PLANT

The following is a detailed description of plants of the new cultivar approximately three months in age (3 cuttings growing in 25-cm containers) under unheated greenhouse conditions with ambient light in Liss, Hampshire, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous tuberous perennial, grown primarily for use in baskets and containers.

*Plant habit*.—Compact, mounded and well-branched habit without cane production in its first year of growth.

*Flowering period*.—From May to October.

*Height and spread*.—Reaches about 25 cm in height and about 25 cm in spread.

*Cold hardiness*.—U.S.D.A. Zone 10.

*Diseases and pests*.—No susceptibility or resistance to diseases or pests has been observed.

*Root description*.—Fleshy to fibrous.

*Tubers*.—Tuber production was not observed on the plants available for data collection.

*Growth rate*.—Semi-vigorous; less vigorous than the cultivar 'Yasped'.

*Propagation*.—Terminal stem cuttings.

Stem description:

*Stem size*.—Average of 25 cm in length and 8 mm in width with lateral branches about 12 cm in length and 5 mm in width.

*Stem shape*.—Round, solid.

*Stem color*.—187B on exposed side, 146A on shaded side.

*Stem surface*.—Smooth, and covered with a few colorless hairs lenticels absent.

*Internode length*.—Up to 12 mm.

*Branching habit*.—Freely branched.

*Branching angle at emergence*.—Approximately 45° to horizontal.

Foliage description:

*Leaf shape*.—Lanceolate, strongly asymmetric with one side narrowly ovate and the other side is narrowly cordate and wider.

*Leaf division*.—Entire.

*Leaf base*.—Cordate.

*Leaf apex*.—Acuminate.

*Leaf venation*.—Pinnate, color 137C on upper surface and 143B on lower surface.

*Leaf margins*.—Irregular serrate with short bristles emerging from tips of the teeth.

*Leaf attachment*.—Petiolate.

*Leaf arrangement*.—Alternate.

*Leaf surface*.—Upper surface; slightly glossy and covered with very occasional scattered short colorless hairs, lower surface; slightly glossy and covered with very occasional scattered short colorless hairs mainly on midrib.

*Leaf color*.—Upper surface; N137A, lower surface; 183C.

*Leaf size*.—Average of 12.5 cm in length and 5.5 cm in width.

*Leaf fragrance*.—None.

*Petioles*.—About 2.0 to 3.5 cm in length and 3.5 mm in width, surface is sparsely pubescent with simple translucent hairs.

*Stipules*.—Narrowly triangular in shape, 138B to 138C to almost translucent in color and rapidly becoming dry and papery, about 5 mm in length and 7 mm in width.

Flower description:

*Inflorescence type*.—3 flowered cymes produced sequentially in the axils of the upper leaves, monoecious with semi-double male flowers and single female flowers.

*Inflorescence number*.—Up to 4 per flowering stem.

*Peduncles*.—Up to 3.8 cm in length and 3 mm in width, color; 180B to 180C on exposed side, 179C on shaded side, surface is glabrous.

*Flower persistence*.—Self-cleaning.

*Flower type*.—Male flowers semi-double, female flowers single.

*Flower longevity*.—Long lived; each flower lasting an average of 10 days.

*Flower fragrance*.—None.

*Flower number*.—3 per inflorescence, up to 12 per stem.

*Flower aspect*.—Upward and outward.

*Bracts*.—2, rounded in shape, obtuse apex, up to 1 cm in length and 1.3 cm width, color is 180A, covered with bristly hairs on upper portion.

Male flowers:

*Pedicels*.—Up to 2.6 cm in length and 1.5 mm in width, color; 180B to 180C on exposed side, 179C on shaded side, glabrous surface.

*Flower buds*.—Flattened broad ovoid in shape, up to 2.8 cm in length and 1.5 cm in width, color is 8D to 49A and 49B on outermost tepal.

*Flower size*.—Up to 4.2 cm in length and 7.5 cm in width.

*Tepals*.—4 in number (2 inner and 2 outer), outer tepals; ovate to elliptic in shape, obtuse apex, rounded base, average of 4.2 cm in length and 2.2 cm in width, glabrous and smooth surface, entire margin, color; outer surface is 46D to 47D, inner surface is 47C to 18D and bordered with 47C to 47D, inner tepals; narrow to ob-elliptic in shape, obtuse apex, cuneate base, up to 3.5 cm in length and 1.1 cm in width, surface is glabrous and smooth on both surfaces, entire margin, color; outer surface is 18D and flushed with 47C to 47D, inner surface is 18D and bordered with 47C to 47D.

*Corolla form*.—Flared, tepals are un-fused.

*Stamens*.—Numerous and deformed and becoming petaloid in varied formations; ob-elliptic in shape, often twisted with a narrow cuneate base and obtuse apex, 1.8 cm in length and 5 mm in width, color at base is 14B to 14C then becomes 43D at the apex, filaments and anthers are not defined, no pollen present.

Female flowers:

*Pedicels*.—Average 3.3 cm in length and 1.5 mm in width, 180B to 180C in color on exposed side, 179C in color on shaded side, glabrous surface.

*Flower buds*.—Flattened ovoid in shape, about 2.9 cm in length and 1 cm in width, color is 8D and becoming 49A to 49B at the outermost tepal.

*Flower size*.—About 4 cm in length (excluding ovary) and 5.5 cm in width.

*Tepals*.—5 in number (3 inner and 2 outer), outer tepals; elliptic in shape, acute apex, rounded base, average of 3 cm in length and 1.5 cm in width, glabrous and smooth surface, entire margin, color; outer surface is 46D to 47D, inner surface is 47C to 18D and bordered with 47C to 47D, inner tepals; narrow ob-elliptic in shape, obtuse to acute apex, narrow cuneate base, up to 3.5 cm in length and 1.4 cm in width, glabrous and smooth surface, entire margin, color; outer surface is 18D and bordered with 47C to 47D, inner surface is 18D and slightly tinged with 47C to 47D at the apex and edges.

*Corolla form*.—Flared, tepals are un-fused.

*Styles*.—3 in number, cylindrical, connate at base for <1 mm, about 2 mm in length and 1 mm in diameter, 14D in color.

*Stigmas*.—Bifid in shape, stigmatic surfaces twisted around extensions of the style with limited access to the stigmas for pollination, lobes about 4 mm in length and 1 mm in width, 14B in color.

*Ovaries*.—Inferior, triangular in cross section with angles unequally winged, about 1.1 cm in length and 9 mm in width (excluding wings), color is 145B to 145C.

*Seed*.—No seed has been observed to date; male flowers are sterile and the female flowers have not been observed to cross-pollinate with other cultivars that are growing in proximity.

It is claimed:

1. A new and distinct cultivar of *Begonia* plant named 'YANTANA' as herein illustrated and described.

* * * * *